United States Patent [19]  [11] Patent Number: 4,634,791
Meier et al.  [45] Date of Patent: Jan. 6, 1987

[54] ARYLAMINE DERIVATIVES WHICH CAN BE INCORPORATED AS CO-POLYMERIZED UNITS IN UNSATURATED RESINS, THE PREPARATION OF THESE DERIVATIVES AND THEIR USE AS CURING ACCELERATORS

[75] Inventors: Helmut-Martin Meier, Hattingen; Rolf Dhein, Krefeld; Jens Winkel, Cologne; Gerhard Klein, Monheim; Werner Klöker, Krefeld, all of Fed. Rep. of Germany

[73] Assignee: Bayer Aktiengesellschaft, Leverkusen, Fed. Rep. of Germany

[21] Appl. No.: 676,485

[22] Filed: Nov. 29, 1984

[30] Foreign Application Priority Data

Dec. 13, 1983 [DE] Fed. Rep. of Germany ....... 3345104

[51] Int. Cl.⁴ .............................................. C07C 125/06
[52] U.S. Cl. ..................................... 560/163; 560/25; 560/115
[58] Field of Search .......................... 560/25, 115, 163

[56] References Cited

U.S. PATENT DOCUMENTS 4,078,015 3/1978 Leitheiser et al. .................. 560/25
4,161,596 7/1979 Cowherd et al. .................. 560/115
4,504,628 3/1985 Johnson ............................. 560/163

Primary Examiner—Harry Wong, Jr.
Attorney, Agent, or Firm—Connolly and Hutz

[57] ABSTRACT

Compounds of the formula

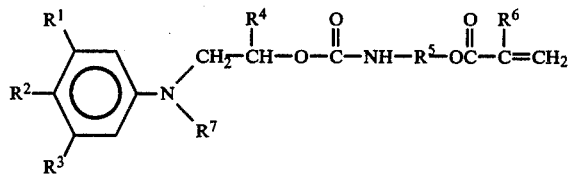

are suitable as curing accelerators which can be incorporated into ethylenically unsaturated, cold-curable resins.

2 Claims, No Drawings

ARYLAMINE DERIVATIVES WHICH CAN BE INCORPORATED AS CO-POLYMERIZED UNITS IN UNSATURATED RESINS, THE PREPARATION OF THESE DERIVATIVES AND THEIR USE AS CURING ACCELERATORS

The invention relates to N,N-disubstituted arylamine derivatives which can be incorporated as copolymerised units in unsaturated resins, a process for their preparation by reacting unsaturated isocyanates with N,N-disubstituted arylamines, wherein at least one nitrogen substituent is a β-hydroxylalkyl group, and their use as curing accelerators for ethylenically unsaturated resins, which can be cold-cured with peroxides, such as acrylates, methacrylates and unsaturated polyester resins, which can be processed to give, for example, fillers, mortar or tooth-filling media.

It is known that moulding compositions based on cold-curable polyester cast resins can be cured using N,N-dialkylarylamines as polymerisation accelerators (U.S. Pat. No. 2,480,928). It is also known that unsaturated polyesters can be prepared with the incorporation of N,N-bis-(β-hydroxyalkyl)-arylamines, and moulding compositions based on these materials can be cured in the cold, in the presence of diethyl peroxides (German Patent Specification No. 919,431). It is furthermore known that N,N-bis-(β-hydroxyalkyl)-arylamines can be reacted with dicarboxylic acids to give a polyester, or with diisocyanates to give a polyurethane, and unsaturated polyester resin materials can be added to the resulting products, as curing accelerators (DE-OS (German Published Specification) No. 1,943,954 and German Patent Specification No. 1,643,972). DE-OS (German Published Specification) No. 3,202,090 and EP-OS (European Published Specification) No. 84,784 also disclose that primary arylamines can be reacted, in a first stage, with bis epoxides and, in a second stage, with monoepoxides to give oligomeric curing accelerators, and these can be used for curing ethylenically unsaturated compositions.

The stated accelerators which are dissolved freely in the resin can migrate and can be extracted both before and after the curing process, or they have a low reactivity owing to their polymeric character.

It is an object of the invention to provide accelerators which do not have the disadvantages described above and which are added in monomolecular form to the resins and are incorporated in these during the during process.

The present invention relates to compounds of the formula I

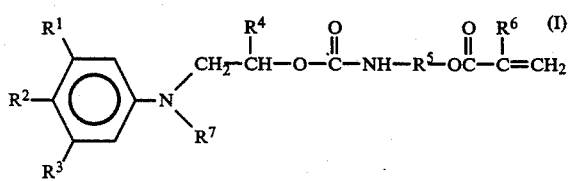

wherein $R^1$ to $R^3$ represent hydrogen, $C_1$–$C_{18}$-alkyl, $C_5$–$C_8$-cycloalkyl, $C_6$–$C_{14}$-aryl or halogen, $R_4$ represents hydrogen, $C_1$–$C_{18}$-alkyl or $C_5$–$C_8$-cycloalkyl, $R_5$ represents $C_1$–$C_{18}$-alkylene, $C_5$–$C_8$-cycloalkylene or $C_6$–$C_{14}$-arylene, $R_6$ represents hydrogen or $C_1$–$C_4$-alkyl and $R^7$ represents a saturated or unsaturated, optionally OH-substituted hydrocarbon radical having 1–18 C atoms or the radicals

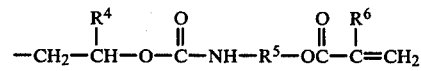

having the meaning given above for $R^4$ to $R^6$.

Preferably, $R^1$ to $R^4$ and $R^6$ denote hydrogen or methyl, $R^5$ denotes $C_2$ to $C_8$-alkylene and $R^7$ denotes methyl or the radical

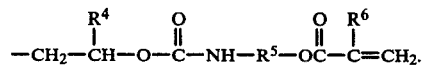

The acrylate groups of the compounds of the formula I are copolymerisable with ethylenically unsaturated compounds.

The compounds of the formula I are obtained by a process in which a tertiary amine of the formula II

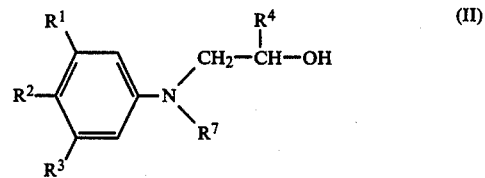

is reacted with an isocyanate of the formula III

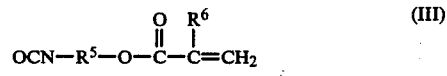

wherein $R^1$ to $R^7$ have the abovementioned meanings, at 20° to 120° C., preferably 60°–100° C.

In particular, equivalent amounts of II and III are reacted in the presence of a heavy metal salt, a tertiary amine or an alkali metal alcoholate or alkaline earth metal alcoholate as a catalyst.

The synthesis route for isocyanates of the formula (III) are described in, for example, U.S. Pat. No. 2,718,516 and U.S. Pat. No. 2,821,544.

In general, isocyanates of the formula (III) can also be obtained by reacting dihydrooxazines, which may be present as acid adducts, with phosgene at −20° to +20° C. in a water-immiscible solvent, in the presence of an aqueous solution of a base, the dihydrooxazines having the general formula

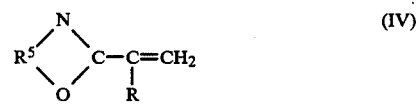

Dihydrooxazines (IV) obtained from N-hydroxymethylamides of the general formula

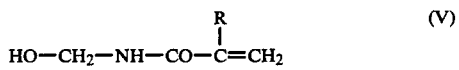

and an olefin can be prepared by the process described in Liebigs Annalen 697, pages 171-180 (1966).

The compounds of the formula I are preferably employed in an amount of from 0.008 to 0.4, in particular 0.04 to 0.2, % by weight of tertiary amine nitrogen, relative to resin to be cured.

The compounds of the formula I are in general highly viscous products. To improve their handling, they are dissolved—advantageously in the course of the preparation process—in suitable solvents or solvent mixtures. Preferred solvents are monomers which are copolymerisable with the polyester, such as styrene, -methyl styrene or esters of methacrylic acid. In addition, limited amounts of solvents which are inert to the polymerisation, such as n-butyl acetate, cyclohexanone or ethylene glycol dimethyl ether, can be used concomitantly. In this form, the accelerators can readily be metered into the resins in any concentration.

Resins which can be cured using the compounds I according to the invention are all ethylenically unsaturated compounds or mixtures which can be polymerised in the presence of diacyl peroxides, preferably unsaturated polyester resins and acrylic resins.

"Unsaturated polyester resins" are mixtures of 30 to 75 parts by weight of $\alpha,\beta$-ethylenically unsaturated polyesters and 70 to 25 parts by weight of unsaturated monomers which are copolymerisable with these. They are described in, for example, J. R. Lawrence, "Polyester Resins", Reinhold Publ. Corp., New York 1960, page 18 et seq., and in Kunststoff-Handbuch (Plastics Handbook), vol. VIII ("Polyester"), Carl Hanser Verlag, Munich 1973, pages 247-312.

A preferred monomer is styrene.

Other preferred copolymerisable monomers are listed in the paragraph following the next one.

"Acrylic resins" in the context of the invention are polyurethanes, polyepoxides, polyols, polyether-polyols or polyesters which contain (meth-)-acryloyloxy groups. These acrylic resins are known.

In order to reduce the viscosity or increase the reactivity or to achieve special properties, the above-mentioned "acrylic resins" can also be mixed with copolymerisable olefinically unsaturated monomers, for example with (meth-) acrylates of monohydric alcohols, hydroxyalkyl (meth) acrylates, (meth-) acrylamides, styrene, $\alpha$-methylstyrene, styrenes which are substituted in the nucleus by alkyl groups, divinylbenzene, (meth-) acrylonitrile, vinyl chloride, vinylidene chloride, vinyl ethers, vinyl acetate or their mixtures. It is of course also possible to polymerise at least one $\alpha,\beta$-monoolefinically unsaturated monomer, for example of the type stated above, in the presence of the compounds according to the invention, of the formula I.

Before the curing process, polymerisation initiators, preferably diacyl peroxides or percarbonates, are added to the resins, in amounts of from 1 to 10% by weight, relative to the resin to be cured. Examples of preferred initiators are diacetyl peroxide, dibenzoyl peroxide, di-p-chlorobenzoyl peroxide, phthaloyl peroxide, succinyl peroxide, dilauroyl peroxide, acetylcyclohexanesulphonyl peroxide, isopropyl percarbonate, cyclohexyl percarbonate and bis-(4-tert.-butylcyclohexyl) percarbonate.

The resin compositions to be hardened can contain the customary fillers, pigments, stabilisers and disinfectants. For use in the dental field, both organic fillers, such as pulverised polyacrylates, and inorganic fillers, such as pulverised quartz or glass or silicon dioxide or aluminium oxide powder, are suitable.

According to the invention, all types of mouldings can be cured in the cold, and can be employed in a very large variety of areas of the construction industry, electrical industry and boat building, and in the automobile industry.

EXAMPLES

Preparation of accelerator 1

0.1% By weight of dibutyl-tin dilaurate was added to a mixture of 1 mol of N-methyl-N-hydroxyethyl-3,5-dimethylaniline and 1 mol of (1-isocyanato-2,3-dimethyl)-propyl acrylate in the absence of moisture, and the mixture was stirred for 6 hours at 60° C.

IR (cm$^{-1}$): no isocyanate absorption at 2275-2250, Absorption at 3350, 1730, 1710 and 1640.

Preparation of accelerator 5

Using the above method, 1 mol of N,N-bis-$\beta$-hydroxyethyl)-p-toluidine and 2 mol of (1-isocyanato)-ethyl methacrylate were reacted.

IR (cm$^{-1}$): no isocyanate absorption at 2275-2250, Absorption at 3350, 1730, 1680 and 1640.

The accelerators 2, 3 and 4 were prepared analogously to 1 and 2, from 1 mol of N-methyl-N-(2-hydroxypropyl)-3,5-dimethylaniline and 1 mol of (1-isocyanato-2,3-dimethyl)-propyl acrylate (2), 1 mol of N-methyl-N-(2-hydroxypropyl)-3,5-dimethylaniline and 1 mol of (1-isocyanato)-ethyl methacrylate (3) and 1 mol of N,N-bis-(2-hydroxypropyl)-3,5-dimethylaniline and 2 mol of (1-isocyanato)-ethyl methacrylate (4).

Accelerator A

Accelerator A is a polycondensation product of N,N-bis(2-hydroxypropyl)-p-toluidine and adipic acid (DE-OS (German Published Specification) No. 3,202,090).

Preparation of unsaturated polyester resins

Polyester resin I

A polyester was prepared from 89 mol of diethylene glycol, 13 mol of ethylene glycol, 98.1 mol of maleic anhydride and 42.1 mol of dicyclopentadiene, by melt condensation. The resin was then dissolved in styrene to give a 63% strength by weight solution, and was stabilised with 0.04% by weight of chloranil and 0.01% by weight of copper naphthenate, the percentages in each case being relative to the polyester resin. The polyester resin had a viscosity of 480 mPas (measured at 25° C.) and an acid number of 10.

Polyester resin II

Polyester II is an unsaturated polyester resin consisting of 2981 kg of maleic anhydride, 1930 kg of phthalic anhydride, 2121 kg of diethylene glycol and 1938 kg of propylene glycol, dissolved to give a 60% strength by weight solution in styrene and having a viscosity of 270-370 mPa.s, an iodine number of less than 2 and a density of 1.1 g/cm$^3$.

Determination of the reactivity

Cold-curable cast resin compositions were prepared using the accelerators 1 to 5 and A and the polyester resins I and II. The content of aromatically bonded nitrogen in the cold-curing resin at the stated concentrations makes it possible to compare the reactivity of the individual accelerators. The reactivity was determined by curing the accelerator/resin mixture at an initial temperature of 25° C., using 2% of commercially available benzoyl peroxide paste (50% benzoyl peroxide content).

The gelling time, curing time and maximum temperature were determined in accordance with DIN 16,945.

| Accelerator | % in the resin | % N in the resin | Gelling time (min) | Curing time (min) | max. Temperature (°C.) |
|---|---|---|---|---|---|
| Curing in polyester resin I | | | | | |
| 1 | 1.58 | 0.064 | 5.9 | 8.8 | 110 |
| 2 | 1.65 | 0.064 | 6.8 | 9.8 | 110 |
| 3 | 1.58 | 0.064 | 5.8 | 8.6 | 103 |
| 4 | 2.20 | 0.064 | 25.6 | 32.8 | 105 |
| 5 | 2.08 | 0.064 | 24.0 | 30.2 | 118 |
| A (comparison) | 2.0 | 0.064 | 11.0 | 17.2 | 110 |
| Curing in polyester resin II | | | | | |
| 2 | 1.55 | 0.060 | 3.2 | 5.9 | 141 |
| 5 | 1.96 | 0.060 | 8.8 | 11.7 | 153 |
| A (comparison) | 1.85 | 0.060 | 4.3 | 7.0 | 144 |

We claim:
1. Compounds of the formula

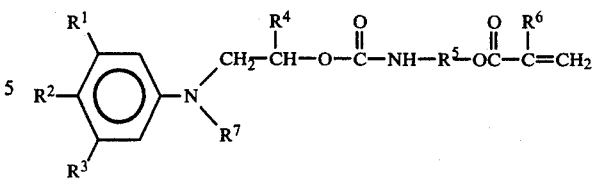

wherein
$R^1$ to $R^3$ represent hydrogen, $C_1-C_{18}$-alkyl, $C_5-C_8$-cycloalkyl, $C_6-C_{14}$-aryl or halogen,
$R^4$ represents hydrogen, $C_1-C_{18}$-alkyl or $C_5-C_8$-cycloalkyl,
$R^5$ represents $C_1-C_{18}$-alkylene, $C_5-C_8$-cycloalkylene or $C_6-C_{14}$-arylene,
$R_6$ represents hydrogen or $C_1-C_4$-alkyl and
$R^7$ represents hydrogen, a saturated or unsaturated hydrocarbon radical having 1-18 carbon atoms, a hydroxy-substituted saturated or unsaturated hydrocarbon radical having 1 to 18 carbon atoms, or the radical

having the meaning given above for $R^4$ to $R^6$.

2. Compounds according to claim 1 wherein $R^1$ and $R^4$ and $R^6$ denote methyl or hydrogen, $R^5$ denotes $C_2-C_8$-alkylene and $R^7$ denotes methyl or the radical

having the meaning given above for $R^4$ to $R^6$.

* * * * *